(12) United States Patent
Spina et al.

(10) Patent No.: US 10,898,160 B2
(45) Date of Patent: Jan. 26, 2021

(54) ACOUSTIC MONITORING SYSTEM, MONITORING METHOD, AND MONITORING COMPUTER PROGRAM

(71) Applicant: KONINKLIJKE PHILIPS N.V., Eindhoven (NL)

(72) Inventors: Gabriele Spina, Eindhoven (NL); Albertus Cornelis Den Brinker, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 704 days.

(21) Appl. No.: 15/534,627

(22) PCT Filed: Nov. 27, 2015

(86) PCT No.: PCT/EP2015/077858
§ 371 (c)(1),
(2) Date: Jun. 9, 2017

(87) PCT Pub. No.: WO2016/091612
PCT Pub. Date: Jun. 16, 2016

(65) Prior Publication Data
US 2017/0325779 A1    Nov. 16, 2017

(30) Foreign Application Priority Data
Dec. 12, 2014 (EP) ..................... 14197657

(51) Int. Cl.
*A61B 7/04*    (2006.01)
*A61B 5/00*    (2006.01)
(Continued)

(52) U.S. Cl.
CPC .............. *A61B 7/04* (2013.01); *A61B 5/0205* (2013.01); *A61B 5/6823* (2013.01); *A61B 5/725* (2013.01);
(Continued)

(58) Field of Classification Search
None
See application file for complete search history.

(56) References Cited

U.S. PATENT DOCUMENTS 7,751,878 B1    7/2010  Merkle et al.
8,641,631 B2    2/2014  Sierra et al.
(Continued)

FOREIGN PATENT DOCUMENTS

CN    102302373 A    1/2012
WO    2007052108 A2   5/2007

OTHER PUBLICATIONS

Ghaderi F. et al, "Localizing Heart Sounds in Respiratory Signals Using Singular Spectrum Analysis", IEEE Transactions on Biomedical Engineering, IEEE Service Center, Piscataway, NJ, USA, vol . 58, No. 12, Dec. 12, 2011 (Dec. 12, 2011), pp. 3360-3367, XP011408578, ISSN: 0018-9294.
(Continued)

*Primary Examiner* — Michael R Bloch

(57) ABSTRACT

The present invention relates to a system (100) and method (800) capable of indirectly monitoring respiratory and cardiac variables. A decomposition technique on time-series of features extracted from the chest audio signal $\alpha(t)$ is proposed. The proposed monitoring system (100) may acquire the acoustic signal on the chest of a subject (140) by means of a wearable transducer (150). The proposed system may estimate a number of physiological variables such as flow estimates, respiration rate, inspiration and expiration markers and cardiac related variables. Cough and apnea detection, adventitious sound recognition, activities performed, and information about energy estimation and the status of a monitored subject can be derived as well.

8 Claims, 9 Drawing Sheets

(51) Int. Cl.
  *A61B 7/00* (2006.01)
  *A61B 5/0205* (2006.01)
  *A61B 5/08* (2006.01)
  *A61B 5/024* (2006.01)
  *A61B 5/087* (2006.01)

(52) U.S. Cl.
  CPC .......... *A61B 5/7264* (2013.01); *A61B 5/7425* (2013.01); *A61B 7/003* (2013.01); *A61B 5/02438* (2013.01); *A61B 5/087* (2013.01); *A61B 5/0816* (2013.01); *A61B 5/0823* (2013.01); *A61B 5/0826* (2013.01)

(56) References Cited

U.S. PATENT DOCUMENTS

| | | | |
|---|---|---|---|
| 2003/0229289 A1* | 12/2003 | Mohler | A61B 5/04023 600/508 |
| 2006/0084877 A1 | 4/2006 | Ujhazy et al. | |
| 2006/0253209 A1 | 11/2006 | Hersbach et al. | |
| 2007/0118054 A1* | 5/2007 | Pinhas | A61B 5/1104 600/587 |
| 2010/0087747 A1 | 4/2010 | Lo et al. | |
| 2011/0002951 A1 | 1/2011 | Lo et al. | |
| 2011/0066041 A1 | 3/2011 | Pandia et al. | |
| 2011/0092839 A1 | 4/2011 | Alshaer et al. | |
| 2011/0295138 A1 | 12/2011 | Lai et al. | |
| 2012/0004749 A1 | 1/2012 | Abeyratne et al. | |
| 2012/0157870 A1 | 6/2012 | Derkx | |
| 2012/0184825 A1* | 7/2012 | Ben David | A61B 7/003 600/301 |
| 2012/0242501 A1 | 9/2012 | Tran | |
| 2012/0253216 A1 | 10/2012 | Fu et al. | |
| 2012/0263315 A1 | 10/2012 | Hiroe | |
| 2013/0331722 A1 | 12/2013 | Rodriguez-Villegas et al. | |
| 2014/0126732 A1* | 5/2014 | West | H04R 1/46 381/67 |
| 2014/0275809 A1 | 9/2014 | Reinisch | |
| 2015/0265206 A1 | 9/2015 | Sheinkopf et al. | |

OTHER PUBLICATIONS

Yildirim I. et al., "Automated respiratory phase and onset detection using only chest sound signal", Engineering in Medicine and Biology Society, IEEE, 2008.

Loudon R. et al., "Lung sounds", American Review of Respiratory Disease, vol. 130(4), pp. 663 to 673 (1984).

Nield M. et al., "Comparison of breathing patterns during exercise in patients with obstructive and restrictive ventilatory abnormalities", Journal of Rehabilitation Research and Development, vol. 40(5), pp. 407 to 414 (2003).

Nici L. et al., "American thoracic society/European respiratory society statement on pulmonary rehabilitation", American Journal of Respiratory and Critical Care Medicine, vol. 173(12), pp. 1390 to 1413 (2006).

Mead J., "Control of respiratory frequency", Journal of Applied Physiology, vol. 15(3), pp. 325 to 336 (1960).

Johnson B. et al., "Emerging concepts in the evaluation of ventilatory limitation during exercise", Chest, vol. 20 116(2), pp. 488 to 503 (1999).

Silva A. et al., "Aerobic exercise training improves autonomic nervous control in patients with COPD", Respiratory Medicine, vol. 103(10), pp. 1503 to 1510 (2009).

Chuah J. et al., "Automated Respiratory Phase Detection by Acoustical Means", Proc. SCI, pp. 228 to 231 (2000).

Hill B., "Development of an Acoustic Respiratory Monitor", Department of Electrical and Computer Engineering, University of Utah, 2011.

Ertel P. et al., "Stethoscope acoustics. II. Transmission and filtration patterns", Circulation, vol. 34, pp. 899 to 909 (1966).

Lin I. et al., "A signal-noise separation algorithm for the estimation of respiratory rate from breath sound", ICICS (International Conference on Information, Communications and Signal Processing) 2011, Singapore.

National Institute for Health and Clinical Excellence, Clinical guideline 101: Chronic Obstructive Pulmonary Disease, London, Jun. 2010.

* cited by examiner

ACOUSTIC MONITORING SYSTEM, MONITORING METHOD, AND MONITORING COMPUTER PROGRAM

CROSS-REFERENCE TO PRIOR APPLICATIONS

This application is the U.S. National Phase application under 35 U.S.C. § 371 of International Application Serial No. PCT/EP2015/077858, filed on 27 Nov. 2015, which claims the benefit of European Application No. 14197657.1, filed on 12 Dec. 2014. These applications are hereby incorporated by reference herein.

FIELD OF THE INVENTION

The invention relates to a monitoring system, a monitoring method, and a monitoring computer program.

BACKGROUND OF THE INVENTION

The need to reduce hospitalization and lengthy hospital stays calls for a paradigm shift from managing patients in the hospital towards the home environment. It is therefore desirable to develop new technologies and service concepts that permit patient monitoring and management at home under the remote guidance of the caregiver. E.g. monitoring COPD patients at home and proper early interventions reduce the number of acute exacerbations and hospital admission, leading to cost savings in the overall health spending. Further, the availability of telemonitoring provides caregivers with increased reassurance to discharge patients earlier from hospitals. Consequently, the number of days that patients spend in hospitals can be reduced. In addition, the use of unobtrusive and wearable sensors provides for continuous monitoring of daily changes in a patient's vital data generating further knowledge on the pathophysiology of the disease and a better understanding of the disease trends.

In the article "Automated respiratory phase and onset detection using only chest sound signal" by I. Yildirim et al., Engineering in Medicine and Biology Society, IEEE (2008), the problem of detecting phase onsets of normal lung sounds is investigated. Prior signal information in both time and frequency from the chest sound are exploited to isolate the lung component of the sound and the quasi-periodicity of its short-term energy is used to develop a configuration of non-linear filters and bandpass filters to estimate the respiratory phase onsets. Chest sounds are modeled as the sum of heart sound, lung sound, and background noise and the filters designed accordingly. In the presence of additional sound components, such as, e.g., sounds related to pulmonary diseases, the filtering bock however needs to be re-designed. The method has to be modified as well to deal with variable respiratory patterns such as during swallowing. The information about the respiration phases and onset are captured in the zero crossings. This is not robust if the signal is floating. Moreover, since the method strongly depends on the short-term energy of the signal, the phase segmentation results are strongly influenced by the amplitude of the input signal.

US 2014/0275809 A1 discloses a method for localizing a pattern in a quasi-periodic signal. A rate or frequency of a quasi-periodic signal is estimated, a search window is defined, and a portion of the quasi-periodic signal in a search window is cross-correlated with a template signal pattern to be matched to produce a second maximum that is defined by the controller as a new starting position. The new starting position is stored.

U.S. Pat. No. 8,641,631 B2 discloses a method and an apparatus for estimating a respiratory rate of a patient comprising the steps of recording respiratory sounds of the patient, deriving a plurality of respiratory rates from recorded sounds using a plurality of respiratory rate estimation methods and applying a heuristic to the plurality of derived respiratory rates, the heuristic selecting one of the derived respiratory rates. The selected respiratory rate is the estimated respiratory rate.

US 2012/0242501 A1 discloses a heart monitoring system for a person including one or more wireless notes; and a wearable appliance in communication with the one or more wireless notes, the appliance monitoring vital signs.

CN 102 302 373 A discloses a method for detecting heart sound signal feature points based on multiplexing multi-resolution wavelet transformation.

Ghaderi F. et al., "Localizing Heart Sounds in Respiratory Signals Using Singular Spectrum Analysis", IEEE Transactions on biomedical engineering, IEEE Service Center, Piscataway, N.J., USA, vol. 58, no. 12, 12 Dec. 2011, pp. 3360-3367 discloses a method for localizing heart sounds in respiratory signals using a singular spectrum analysis.

US 2011/0295138 A1 discloses a method and system for reliably estimating inspiration-to-expiration ratio for an acoustic physiological signal.

More suitable algorithms and techniques are still needed to deploy chest sounds for continuous monitoring of respiratory and cardiac parameters in an automatic fashion. In particular, more suitable technologies are still necessary to address issues as: low signal-to-noise ratio, different breath sound intensities, phase duration, variable breathing patterns, interferences from non-biological sounds (electromagnetic interference, movement artifacts, environmental noise, etc.), and interference from biological sounds such as the heart beats, abnormal lung sounds, swallowing, coughing, speech.

Moreover, in order to deploy a respiration monitor in real-world applications, it has to be light in order to be worn by the patient and compatible with commonly daily used acquisition systems like smartphones. The bulkiness and awkwardness of a professional stethoscope cup, for example, is not ideal in real-world applications. Furthermore, the use of visible and recognizable medical systems is going to be less accepted by the patients in their everyday life.

SUMMARY OF THE INVENTION

It is an object of the present invention to provide an improved monitoring system, an improved monitoring method, and an improved computer program. In particular, it is desired to improve the existing approaches by making use of a decomposition step to analyze acoustic signals.

In an aspect of the invention, there is provided a monitoring system comprising: an acoustic signal providing unit, providing an acoustic signal indicative of at least one physiological variable of a subject, a feature extraction unit that is configured to provide a detection signal based on a spectral analysis of the acoustic signal, wherein said detection signal is a signal in the time domain that reflects the local structure of the acoustic signal in a simplified form, a detection signal decomposition unit that is configured to decompose the detection signal into at least one detection signal component; and a physiological variable providing unit that is configured to derive said at least one physiological variable from at least one reconstructed physiological signal wherein said reconstructed physiological signal is based on said at least one detection signal component.

The present invention explores the feasibility of monitoring respiratory and cardiac variables indirectly. In an embodiment, indirect monitoring of respiratory and cardiac variables is performed by analyzing acoustic signals. In particular, the present invention relates to the understanding of using a decomposition technique on time-series of features extracted from a subject's chest audio signal. Dedicated software tools compute the estimation of a number of physiological variables such as the respiration rate, inspiration and expiration markers, cardiac related variables and flow estimates. Cough and apnea detection, adventitious sound recognition, activities performed, and information about the status of a monitored subject may be also derived.

In an embodiment, said detection signal decomposition unit is configured to decompose said detection signal by means of a data-driven algorithm. In other words, the algorithm decides ad-hoc or on-the-fly how the signal is to be decomposed, rather than, e.g., applying a bandpass filtering method, where the bands are specified upfront. Because the algorithm is not a-priori fixed in how it decomposes the detection signal, the present invention is less sensitive to irregular components of the signal. Such irregular components might be especially frequent with ill patients. Another origin of irregular components may originate from the fact that an acoustic sensor is continuously placed on the subject's chest, where the subject does not maintain a rest position over the monitoring period, but instead is free to move around.

In an embodiment, said detection signal decomposition unit is configured to decompose said detection signal such that a decomposition of said detection signal is data-driven. In that sense, it may be said that decomposition is not a priori fixed. As noted above, the present invention is less sensitive to irregular components of the signal because a data-driven algorithm is not a-priori fixed in how it decomposes the detection signal, but instead it uses signal features to define the decomposition and because it typically includes a ranking-based stage that allows the rejection of not meaningful components. The said ranking-based stage, in particular, returns a number of components that is not fixed, but based on the characteristics of the input signal.

In an embodiment, said detection signal decomposition unit is configured to perform at least one of a singular spectral analysis (SSA), and/or an empirical mode decomposition (EMD). Singular spectral analysis has the advantage of being generally applicable, and easy to use in an automatic procedure. In general, the above-listed algorithms have the common feature that the analysis can be considered a two-staged approach. In the first step, certain features of the data are collected. Based on these, the actual decomposition is performed. In SSA, these features are the Empirical Orthogonal Functions derived from the lag-covariance matrix which are subsequently used to project the detection signal. In EMD, the local extreme act as features and an iterative procedure is used to extract components based on these extreme.

In an embodiment, said detection signal decomposition unit is configured to decompose said detection signal into a sum of at least a reconstructed physiological signal (e.g. a lung sound signal, a heart sound signal), and a plurality of reconstructed noise signals. Specifically, the embodiment proposes to decompose the detection signal such that more than one reconstructed noise signals is taken into account. In this respect, the embodiment may also account for reconstructed noise signals, which themselves have a specific time-dependent structure (e.g., periodicity).

In an embodiment, said at least one reconstructed physiological signal and/or said plurality of noise signals are based on a plurality of detection signal components from a decomposition algorithm employed by said detection signal decomposition unit, wherein the number of detection signal components in said plurality of detection signal components is not a priori fixed.

In an embodiment, said at least one reconstructed physiological signal corresponds to a plurality of detection signal components, wherein said reconstructed physiological signal is based on said plurality of detection signal components. In particular, the embodiment foresees the possibility of having more than one reconstructed physiological signal influencing the determination of a physiological variable. Having more than one reconstructed physiological signal as input of the same physiological variable providing unit will increase the robustness (and accuracy) of the system.

In an embodiment, said monitoring system is configured to monitor a subject over a time period of at least one hour, ten hours, and/or one day. Consequently, the embodiment specifies a monitoring system capable of continuously monitoring a subject rather than only being able to perform a spot check measurement.

In an embodiment, said acoustic signal providing unit comprises an unobtrusively placed sensor configured to acquire said acoustic signal. In an embodiment, said acoustic signal providing unit comprises a sensor placed on the chest of a subject. By placing the sensor on the chest of a subject under the garments, a patient is more likely to comply with wearing the sensor, because the sensor is not visible and does not obstruct everyday functions of the patient. That way, continuous monitoring is facilitated.

In an embodiment, said acoustic signal providing unit comprises a wearable acoustic transducer. The wearable acoustic transducer may be, e.g., a wearable microphone.

In an embodiment, said acoustic signal providing unit comprises an input unit configured to receive said acoustic signal. Rather than acquiring the acoustic signal by means of a microphone or any other acoustic transducer, the acoustic signal may be recorded or detected beforehand and transmitted to the monitoring system for further analysis. Consequently, the system may be realized as a software solution stored on a device such as a smartphone, to which a patient needs only couple the output of a chest sensor.

In an embodiment, said monitoring system further comprises a calibration unit that is configured to assign said at least one detection signal component to said reconstructed physiological signal. The reconstructed physiological signal may comprise at least one of (i) a flow estimate signal, (ii) a respiratory signal, and/or (iii) a cardiac signal. Since the output of the decomposition unit depends on the decomposition algorithm used, the output may not correspond one-to-one to the respective signals, an additional calibration step may be desirable to identify the signals used for deriving the various physiological variables. The calibration unit may perform a calibration step. The calibration unit may also receive calibration parameters to merely apply the result of a calibration procedure performed by a different unit. It shall be understood that the calibration unit may more generally refer to a mere mapping unit. In particular, the term "calibration unit" does not exclude 1:1-mappings of detection signal components to reconstructed physiological signals.

In an embodiment, said monitoring system further comprises a calibration unit that is configured to assign said at least one detection signal component to said reconstructed physiological signal based on a priori knowledge concerning physiological signals and their features. The a priori knowledge may involve, e.g. features such as, e.g., the signal strength and frequency. Signal strength and frequency are suitable variables to determine the nature of the respective signal component. To that extent, use is made of the fact that heart rate and breathing rate are different, e.g. common ranges for heart rate and respiration rate are 60-100 beat per minute and 16-20 breaths per minute respectively. Further, use may be made of the fact that the sound from the heart has a different amplitude than the sound from breathing.

In an embodiment, said monitoring system further comprises a feature extraction unit configured to provide said detection signal. In an embodiment, said monitoring system further comprises a feature extraction unit configured to provide said detection signal, wherein said feature extraction unit is configured to perform a discrete Fourier transform. When observing the temporal evolution of the breathing signal, it is noticeable that the occurrence of an onset is usually accompanied by an increase of the signal's amplitude. Chest audio signals are both additive (lung, heart sounds and interferences superimpose rather than conceal each other) and oscillatory. Therefore, it is not possible to look for changes by simply differentiating the original signal in the time domain. A number of intermediate signals or features $f_i(t)$ that reflect, in a simplified form, the local structure of the original signal need to be computed for further processing. The result of said further processing is a detection signal $f(t)$. In this embodiment, a feature extraction unit provides $f_i(t)$ as the DFT of the audio signal, but it can be replaced by any detection signal, by replacing the DFT computation by another computational module. For instance, other spectral representation like the Mel Frequency Cepstral Coefficients may be used as well.

In an embodiment, said monitoring system further comprises a feature extraction unit configured to provide said detection signal, wherein said feature extraction unit is configured to perform a discrete Fourier transform, wherein said feature extraction unit is configured to average absolute values of a plurality of frequency bins, wherein said plurality of frequency bins is obtained from performing said discrete Fourier transform.

In an embodiment, said monitoring system further comprises a feature extraction unit configured to provide said detection signal, wherein said feature extraction unit is configured to perform a discrete Fourier transform, wherein said feature extraction unit is configured to average squared values of a plurality of frequency bins, wherein said plurality of frequency bins is obtained from performing said discrete Fourier transform.

In an embodiment, said monitoring system further comprises a pre-processing unit configured to receive said acoustic signal. In an embodiment, said monitoring system further comprises a pre-processing unit configured to receive said acoustic signal, wherein said pre-processing unit is configured to perform a down-sampling step on said acoustic signal. The acoustic signal may be pre-processed by a pre-processing unit to reduce the computational complexity of the further steps. As an example, an audio signal acquired at 44 kHz can be down-sampled to 4 kHz by down-sampling unit.

In an embodiment, said monitoring system further comprises a pre-processing unit configured to receive said acoustic signal, wherein said pre-processing unit comprises a high-pass filter unit configured to apply a high-pass filter to a signal based on said acoustic signal. By applying a high-pass filter low-frequency signals, e.g., with frequencies lower than 50 Hz (e.g. power line hum noise, electrical noise, subject's footsteps while walking), may be attenuated.

In an embodiment, said monitoring system further comprises a pre-processing unit configured to receive said acoustic signal, wherein said pre-processing unit is configured to perform a down-sampling step on said acoustic signal.

In an embodiment, said monitoring system further comprises a pre-processing unit configured to receive said acoustic signal, wherein said pre-processing unit is configured to perform a down-sampling step on said acoustic signal, wherein said pre-processing unit comprises a high-pass filter unit configured to apply a high-pass filter to a signal obtained from said down-sampling step. By applying a high-pass filter low-frequency signals, e.g., with frequencies lower than 50 Hz (e.g. power line hum noise, electrical noise, subject's footsteps while walking), may be attenuated.

In an embodiment, said monitoring system further comprises a display unit configured to display at least one of said acoustic signal and said at least one signal component.

In an embodiment, said monitoring system further comprises a storage unit configured to store at least one of said acoustic signal and said at least one signal component.

In an embodiment, said monitoring system further comprises a reconstructed physiological or noise signal providing unit configured to provide said at least one reconstructed physiological or noise signal. In an embodiment, said monitoring system further comprises a reconstructed physiological or noise signal providing unit configured to provide said at least one reconstructed physiological or noise signal, wherein said reconstructed physiological or noise signal providing unit comprises an output unit.

In another aspect of the invention, there is provided a monitoring method comprising: providing an acoustic signal indicative of at least one physiological variable of a subject, providing a detection signal based on a spectral analysis of the acoustic signal, wherein said detection signal is a signal in the time domain that reflects the local structure of the acoustic signal in a simplified form, decomposing the detection signal into at least one detection signal component; and deriving said at least one physiological variable from at least one reconstructed physiological signal, wherein said reconstructed physiological signal is based on said at least one detection signal component.

In another aspect of the invention, there is provided a monitoring computer program, the computer program comprising program code means for causing the monitoring system to carry out the steps of the monitoring method, when the computer program is run on a computer controlling the monitoring system.

It shall be understood that the monitoring system of claim 1, the monitoring method of claim 26, and the monitoring computer program of claim 27 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
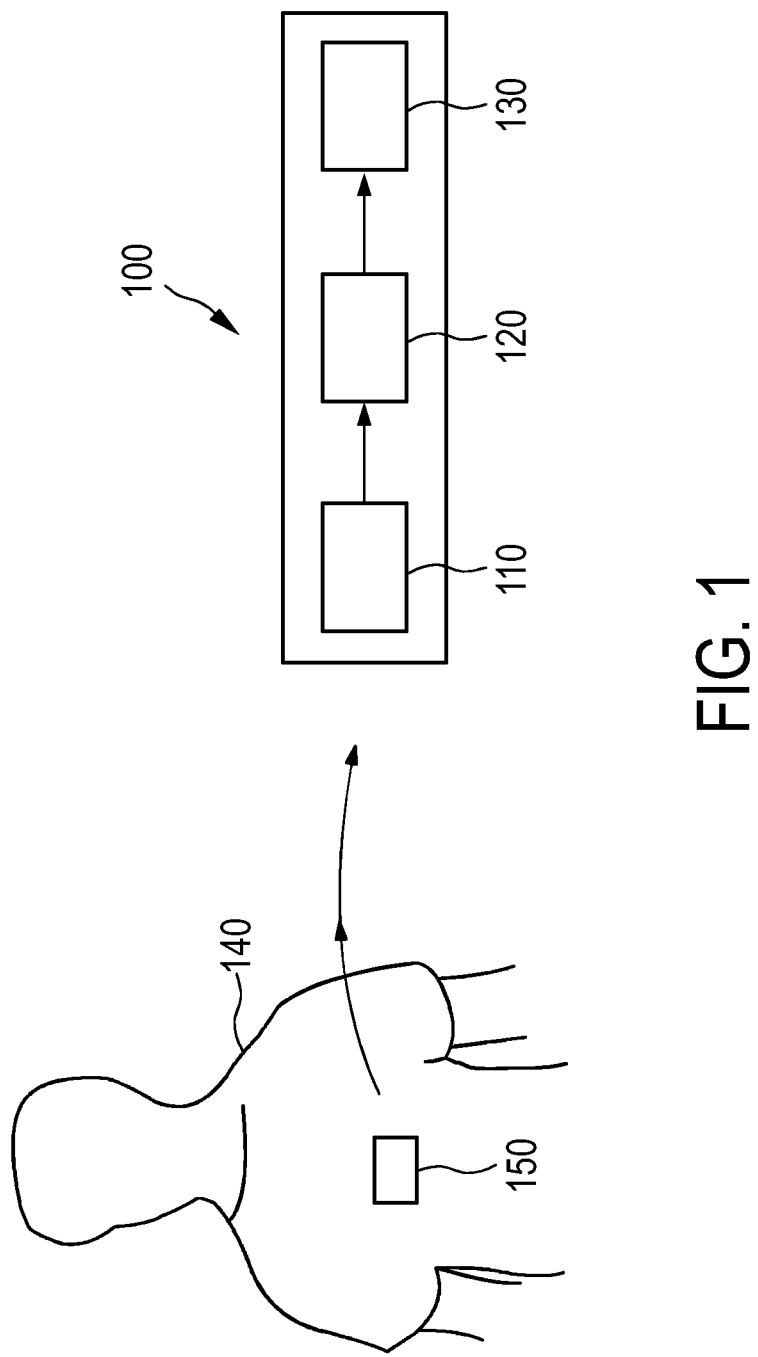
FIG. 1 shows schematically and exemplarily an embodiment of a monitoring system.

The need to reduce hospitalization and lengthy hospital stays strongly calls for a paradigm shift from managing patients in the hospital towards the home environment. It is therefore desirable to develop new technologies and service concepts that permit patients monitoring and management at home under the remote guidance of the caregiver.

E.g. monitoring COPD patients at home and proper early interventions reduce the number of acute exacerbations and hospital admission, leading to cost savings in the overall health spending. Further, the availability of telemonitoring provides caregivers with increased reassurance to discharge patients earlier from hospitals. Consequently, the number of days that patients spend in hospitals can be reduced.

In addition, the use of unobtrusive and wearable sensors provides for continuous monitoring of daily changes in a patient's vital data generating further knowledge on the pathophysiology of the disease and a better understanding of the disease trends.

The complex sonic signals arising in the lungs during respiration are indicative of physiologic and roentgenologic information. Their clinical correlation and the non-invasive nature of their measurements brought them throughout history to be considered a powerful and appealing tool for diagnosis and patients monitoring, as described in the article "Lung sounds" by R. Loudon et al., American Review of Respiratory Disease, volume 130(4), pages 663 to 673 (1984).

Breath sounds originate in the large airways (tracheabronchi) when the flow rate exceeds the threshold associated with the Reynold's number for the airflow geometry. In this circumstance, air velocity and turbulences induce vibrations in the airway walls that are then transmitted through the lung tissue and thoracic wall to the surface, where they may be heard readily with the aid of a stethoscope.

It is a common misconception that air moving through terminal bronchioles and alveoli also contribute to breath sounds. Due to the very large total cross sectional area, the air velocity at this level is however too slow to produce significant turbulence and sound waves. Nonetheless, the sounds that are heard at the periphery of the lung are altered as they pass through pulmonary tissue to the periphery. Pulmonary diseases do also modify the breathing sounds heard at the surface by altering the tonal quality and by either increasing or decreasing the sound transmission through the diseased tissue.

Together with the audio characteristics, breathing is commonly assessed in terms of timing and exchanged flow. For example, a high respiration rate, low fractional inspiration time or low inspiration to expiration time ratio may indicate obstruction of a subject's airways (cf. the article "Comparison of breathing patterns during exercise in patients with obstructive and restrictive ventilatory abnormalities" by M. Nield et al., Journal Of Rehabilitation Research And Development, volume 40(5), pages 407 to 414 (2003)).

Minute ventilation (VE), respiratory frequency (fR), tidal volume (VT), inspiratory time (TI), expiratory time (TE), inspiration to expiration time ratio (TI/TE), total breath time (TTOT), fractional inspiration time (TI/TTOT), mean inspiratory flow, mean expiratory flow, and mean inspiratory flow to expiratory flow are variables commonly measured in the clinical practice.

In chronic obstructive pulmonary disease (COPD), ventilation is often higher than expected because of increased dead-space ventilation, impaired gas exchange, and increased ventilatory demands related to deconditioning and peripheral muscle dysfunction (cf. the article "American thoracic society/European respiratory society statement on pulmonary rehabilitation" by L. Nici et al., American Journal of Respiratory and Critical Care Medicine, volume 173(12), pages 1390 to 1413 (2006)).

The faster respiratory rate in patients with COPD implies also a proportionally greater fall in compliance which shortens the time constant of the respiratory system (cf. the article "Control of respiratory frequency" by J. Mead, Journal of Applied Physiology, volume 15(3), pages 325 to 336 (1960)).

Moreover, monitoring breathing pattern components of patients with obstructive lung disease during daily living activities as well as during training exercises may provide further insight in the role played by dynamic hyperinflation in the genesis of dyspnea, which is often the symptom that bothers patients the most.

The delay of normal emptying of the lungs during expiration due to flow limitation, which is aggravated during exercise (cf. the article "Emerging concepts in the evaluation of ventilatory limitation during exercise" by B. Johnson et al., Chest, volume 116(2), pages 488 to 503 (1999)), leads to dynamic hyperinflation related to the increase in the respiratory frequency. This results in increased work of breathing, increased load on the respiratory muscles, and the intensified perception of respiratory discomfort.

A high TI/TE may provide other information about the status of a monitored subject, for example, may indicate that the subject is currently snoring or speaking. The trend in respiration rate and TI/TE ratio may also be instructive in some applications as for teaching breathing strategies. Direct emphasis on the breathing parameter (in particular on the expiratory time) may be more effective compared with the usual teaching instructions to increase VT or slow fR, since prolonged expiratory times in relation to inspiratory times would likely decrease air trapping and reduce dynamic hyperinflation for those with obstructive ventilatory disorders and provide dyspnea relief.

In the article "Aerobic exercise training improves autonomic nervous control in patients with COPD" by A. Silva et al., Respiratory Medicine, volume 103(10), pages 1503 to 1510 (2009), it has been observed that respiration rate (breathing frequency) reduced after physical training, concomitantly with reduction in dyspnea and improvement in VT. These adjustments in the respiratory pattern may help to explain the improvement of parasympathetic activity after training. Further investigations of manipulation of the timing components of the breathing pattern during low-level exercise and after pulmonary rehabilitation training are then essential. Moreover since dynamic hyperinflation is difficult to measure directly, use of non-invasive measures, such as the timing components of TI/TE and TI/TTOT would be useful.

Despite the obvious benefits of performing continuous respiratory monitoring, the search for an accurate, non-invasive, and non-obtrusive method to continuously monitor all the components of breathing has proven to be long and unsuccessful. Several technologies have been developed in an attempt to fill this clinical gap, but none has gained sufficient physician confidence to become a standard of care. In this regard, inductive plethysmography, fiber optic humidification and capnography are among the most popular technologies. Each of these has advantages and disadvantages, but none has proven to be clearly superior and suitable for continuous monitoring.

Auscultation of the lung sound is an important and simple method to detect various respiratory parameters since it does not affect the natural pattern of respiration, it is not invasive, and it is not expensive.

The estimation of respiratory variables using acoustical means is hindered by several factors such as the non-stationarity and non-linear nature of the respiratory sound signal, the interference of non-biological (60 Hz, environment noise, glitches, etc.) and biological signals (heart beat, swallow, cough, speech and others) and low signal-to-noise (S/N) ratio. Another problem arises when one of the respiratory phases is significantly stronger than the other and abnormal patterns caused by pulmonary diseases.

US 2012/0253216 describes known techniques for isolating respiration phases within an acoustic signal relying on a body mounted sound transducer and peak analysis. The sound transducer is typically placed over the suprasternal notch or at the lateral neck near the pharynx because lung sounds captured in that region typically have a high signal-to-noise ratio and a high sensitivity to variation in flow (cf. the article "Automated Respiratory Phase Detection by Acoustical Means" by J. Chuah et al., Proc. SCI, pages 228 to 231 (2000)).

In addition, an acoustic respiratory monitor was developed in which audio signals were recorded using a microphone placed in a metal precordial stethoscope cup and affixed to the neck with a double-stick disc just below the larynx and above the supersternal notch (cf. the Ph.D. thesis "Development of an Acoustic Respiratory Monitor" by B. Hill, Department of Electrical and Computer Engineering, University of Utah, 2011). The stethoscope cup used was a heavy precordial metal cup designed to amplify signals detected within the cup and attenuate external signals from entering the cup.

Acoustics of the stethoscope cup can change depending on the placement of the cup on the skin, the tightness of the skin within the cup, and the placement of the stethoscope cup on the trachea affecting the performance of the system (cf. the article "Stethoscope acoustics. II. Transmission and filtration patterns" by P. Ertel et al., Circulation, volume 34, pages 899 to 909 (1966)). This system and method used to analyze the tracheal sounds are also sensitive to the microphone used. Indeed, during the experiment, one data set was discarded because it was recorded with a different microphone than for the other recordings.

The use of a thick metal stethoscope cup helped in the attenuation of the ambient sounds, but the heavy stethoscope is bulky. The weight and awkwardness of the stacked cups is not ideal in real-world applications.

U.S. Pat. No. 8,641,631 proposes to use a piezo-electric film as a transducer on the trachea. This device is used in conjunction with a conventional pulseoximeter. Using a piezo-electric film rather than a conventional microphone inside a stethoscope cup makes the device subject to lower frequency vibrations. In particular, using piezo-electric films, the signal-to-noise ratio is not as high as compared to a conventional microphone inside a stethoscope cup with the consequence to not work well in an acoustically noisy environment. The method to detect respiratory rate (RR) is based on the detection of the frequency of silent intervals in the recorded sounds. It could be deployed in quiet and steady stationary situations (such as, e.g., anesthesia, sleep), but not for a continuous monitoring. The device might further rely heavily on its combined used with a pulse-oximeter.

The systems described so far either are unreliable in the presence of background noise and other body sounds (e.g., heart sounds) or heavily dependent on the performance of dedicated filters. Moreover tracheal-based sensors are visible and then not optimally suitable for continuous monitoring in a real-life scenario.

In the article "Automated respiratory phase and onset detection using only chest sound signal" by I. Yildirim et al., Engineering in Medicine and Biology Society, IEEE (2008), the problem of detecting phase onsets of normal lung sounds was investigated. Prior signal information in both time and frequency from the chest sound were exploited to isolate the lung component of the sound and the quasi-periodicity of its short-term energy was used to develop a configuration of non-linear filters and bandpass filters to estimate the respiratory phase onsets. Chest sounds were modeled as the sum of heart sound, lung sound, and background noise and the filters designed accordingly. In the presence of additional sound components, such as, e.g., sounds related to pulmonary diseases, the filtering bock however needs to be re-designed. The method has to be modified as well to deal with variable respiratory patterns such as during swallowing. The information about the respiration phases and onset are captured in the zero crossings. This is not robust if the signal is floating. Moreover, since the method strongly depends on the short-term energy of the signal, the phase segmentation results are strongly influenced by the amplitude of the input signal.

In the article "A signal-noise separation algorithm for the estimation of respiratory rate from breath sound" by I. Lin et al., ICICS (International Conference on Information, Communications and Signal Processing) 2011, Singapore, 13 to 16 Dec. 2011, respiratory sounds were recorded over the right side of the chest-wall and used to estimate respiratory rate by means of a threshold-based method that separates the breathing from the background noise. As expected the algorithm performance strongly depends on the recording condition as the estimation accuracy degrades for very noisy background. Moreover, respiration onsets and then respiration timing cannot be monitored.

Performance results for monitoring patients continuously in unconstrained scenarios are available regarding breathing phases recognition and onset detection during controlled tests with healthy subjects. The error in detecting breathing onsets is usually reported as mean and standard deviation of the differences between the estimated onsets and the corresponding actual breathing onsets. For a fully automated system that uses both chest and tracheal sounds an accuracy of 93% (±7%) is reported for phase recognition while the average onset detection error is 118±39 ms. When using only one channel of data (chest sound data) and a more complex detection algorithm the estimation error in expiration onsets for low flow rate is 74±21.9 ms and for medium flow rate is 88.3±29.4 ms. The estimation error in inspiration onsets for low flow rate is 94.1±56.9 ms and for medium flow rate is 69.8±19.9 ms. It has to be noted that the test procedure and the reference system deployed altered both the pattern and the acoustic properties of the signal. The subjects were asked to maintain their respiration at a constant rate while their breathing was monitored on oscilloscope display. The acoustic properties of the signal were modified by the mouth mounted flow transducer used as reference.

The system and methodology described hereby show comparable performances with less variability despite the fact that the focus is not on acquiring ideal audio signals. Accurate detection of breathing onsets is necessary to estimate flow parameters, to investigate cardio-respiratory coordination (i.e., a tendency towards a constant-time relationship between heart beats and respiratory onsets), cardio-ventilatory coupling (i.e., the alignment of the inspiratory onset with the heart beat), and phase synchronization (i.e., the adjustment of heart beats at phases of the respiratory cycles). Moreover accurate detection of phase duration could be used to study if changes in breathing timing parameters are correlated with changes in the disease status of patients affected by cardiopulmonary diseases.

Accurate measurements of respiration patterns and parameters are achieved by means of spirometry devices such as pneumotachographs or by the combined use of nasal cannulae connected to a pressure transducer. Although those direct measurements are accurate, they deploy mechanisms that affect the natural pattern of breathing (i.e. tight-fitting face-masks) or that could miss the detection of mouth breaths (nasal cannulae).

Moreover, application of masks or cannulae around the mouth or nose can be very aversive when dealing with patients suffering from obstructive pulmonary disease. Those systems indeed may increase dyspnea discomfort and cause significant agitation which may hamper the assessment. They are not applicable, then, for continuous, daily measurements.

Pulse-oximetry is a very common and useful monitor because of its ability to continuously measure the blood-oxygen saturation and measure the patient's heart rate. Although it does measure the blood-oxygen saturation it cannot replace direct respiratory monitoring because of its response delay. Moreover in its most common application mode, the sensor is usually placed on the patient's finger limiting the use of the hand. Thoracic-impedance plethysmography uses ECG electrodes on the chest to measure the change in thoracic impedance. Less common is respiratory inductance plethysmography (RIP), which is measured by finding the change of inductance in wires sewn into elastic bands that are placed on the chest and abdomen. Both techniques can be corrupted by body movement of the patient. The use of RIP or piezo chest belts is challenging in subjects with poor postural control, making it difficult to ensure stable positioning of the respiratory inductance bands. Belts add also sensation of chest compression that limit the use in patients suffering from shortness of breath.

Breathing sound analysis is a methodology highly used in common clinical practice due in part to the low cost, unobtrusiveness and ready availability of the measurements. Acoustic analysis of respiration is commonly associated with auscultation of the chest by mean of a stethoscope. This technique is usually used for spot check measurements and patient screening rather than for continuous monitoring. Listening to a patient's breath, indeed, can be laborious and it requires practice and training.

Breath sounds have been analyzed and modeled electronically using computer algorithms to detect respiration parameters. The sound transducer is typically placed over the patient's neck in order to capture tracheal sounds. Once the acoustic signal has been generated, respiration phases are isolated within the acoustic signal and respiration parameter estimates are calculated.

Tracheal sounds offer several advantages compared to chest sounds:
  they are less filtered since the distance from the various sound sources in the upper airways to a sensor on the neck surface is relatively short and without interposition of lung tissue;
  they have distinctly separable respiratory phases;
  they have a high sensitivity to variation in flow;
  they typically have a high signal-to-noise ratio.

On the other hand, diffuse processes that affect most parts of the lungs in pulmonary diseases produce abnormal sounds that are more likely to be better heard throughout the chest-wall. Spotting and analyzing abnormal lung sounds together with respiration timing parameters appears to be extremely relevant for the understanding of the progression of the disease. For example, the proportion of the respiratory cycle occupied by wheezing sounds roughly corresponds to the degree of airway obstruction. To recognize, monitor, and relate the timing of abnormal sounds to breaths duration, the use of tracheal-based sensors is not the best option.

Moreover, acquiring chest sounds is helpful if interested in monitoring also cardiac related parameter as heart rate (HR), heart rate recovery time (HRR), and heart rate variability (HRV). Those are important variables since pulmonary disease are often associated with cardiac autonomic dysfunctions and subjects suffering from pulmonary disease demonstrate frequent abnormalities of cardiac rate and rhythm. In particular, compared to healthy people, they have elevated HR, a lower HRR, and a decreased HRV.

Another important aspect is that systems for continuous monitoring of respiratory and cardiac parameters outside a clinical setting should be unobtrusive. This means that they should be donned or doffed quickly by the wearer, be easy to use, small, light, and require no skin preparation for the sensors to operate with sufficient fidelity. Furthermore, in order to be deployed in everyday life and over extensive periods of time the acoustic transducer should be also not visible and possibly integrated in objects of everyday life (a smartphone for example). This is perhaps the main downside of using a tracheal-sensors attached to the patient's neck. The use of a chest-mounted sensor, placed under the cloths could then overcome this issue.

Current acoustic respiration monitors do not take into account the different nature of sounds arising from diseased lungs. The premise of current respiration monitoring methods is the fact that the chest sound signal is relatively silent during expiration as opposed to inspiration; hence sound intensity might appear an accurate index for distinguishing respiratory phases. In presence of obstructive diseases this is not always true since both inspiratory and expiratory phases could have similar loudness caused by the extra effort needed to breathe out. Moreover diseases may introduce additional sounds that could not be filtered out using standard technique deployed, for example, to remove heart artifacts. Those sounds could become an error source in detecting respiration onsets. On the other hand complex and ad-hoc filtering technique should be avoided in order to keep the applicability as general as possible and not dependent for example on sensor placement or presence of interference sources (for example heart sounds or swallowing events).

More suitable algorithms and techniques are still needed to deploy chest sounds for continuous monitoring of respiratory and cardiac parameters in an automatic fashion. In particular more suitable technologies are still necessary to address issues as: low signal-to-noise ratio, different breath sound intensities, phase duration, variable breathing patterns, interferences from non-biological sounds (electromagnetic interference, movement artifacts, environmental noise, etc.), and interference from biological sounds such as the heart beats, abnormal lung sounds, swallowing, coughing, speech.

Moreover, in order to deploy a respiration monitor in real-world applications, it has to be light in order to be worn by the patient and compatible with commonly daily used acquisition systems like smartphones. The bulkiness and awkwardness of a professional stethoscope cup, for example, is not ideal in real-world applications. Furthermore, the use of visible and recognizable medical systems is going to be less accepted by the patients in their everyday life. The present invention overcomes those issues.

The present invention explores the feasibility of monitoring respiratory and cardiac variables indirectly, e.g., by using a unique, low cost, portable, not visible and flat acoustic sensor connected to a low resources analysis system. The present invention relates to the understanding of using a decomposition technique on time-series of features extracted from a subject's chest audio signal. Dedicated software tools compute the estimation of a number of physiological variables such as the respiration rate, inspiration and expiration markers and cardiac related variables. Cough and apnea detection, adventitious sound recognition, activities performed, and information about the status of a monitored subject may be also derived.

FIG. 1 shows schematically and exemplarily an embodiment of a monitoring system 100 comprising: an acoustic signal providing unit 110, providing an acoustic signal indicative of at least one physiological variable of a subject, a detection signal decomposition unit 120 that is configured to decompose a detection signal into at least one detection signal component, wherein said detection signal is based on said acoustic signal; and at least one physiological variable providing unit 130 that is configured to derive said at least one physiological variable from at least one reconstructed physiological signal, wherein said reconstructed physiological signal is based on at least one detection signal component. Acoustic signal providing unit 110 may receive the acoustic signal indicative of at least one physiological variable of a subject from a sensor 150 placed on the chest of a subject 140. To that extent, sensor 150 may be comprised in acoustic signal providing unit 110. Of course, sensor 150 may also simply transmit the acoustic signal to acoustic signal providing unit 110 by means of a wired or wireless connection.

As described in further detail below, detection signal decomposition unit 120 is configured to decompose said detection signal by means of a data-driven algorithm. In particular, detection signal decomposition unit 120 is configured to decompose said detection signal such that a decomposition of said detection signal is data-driven and in that sense not a priori fixed. To this extent, as described in further detail below, detection signal decomposition unit 120 is configured to perform at least one of a singular spectral analysis, and/or an empirical mode decomposition. Detection signal decomposition unit 120 is configured to decompose said detection signal into one or more components suitable for deriving one or more reconstructed physiological signals (e.g. reconstructed breathing flow signal, reconstructed respiration signal, reconstructed cardiac signal and additional not a-priori-known reconstructed signals).

The at least one reconstructed physiological or noise signal may correspond to a plurality of detection signal components, wherein the number of detection signal components in said plurality of detection signal components is not a priori fixed. Physiological variable providing unit 130 may be configured to derive said at least one physiological variable from at least one reconstructed physiological signal. Monitoring system 100 may be configured to monitor a subject over a time period of at least one hour, ten hours, and/or one day.

Acoustic signal providing unit 110 may comprise an unobtrusively placed sensor configured to acquire said acoustic signal. Specifically, acoustic signal providing unit 110 may comprise a sensor placed on the chest of a subject. Alternatively and/or additionally acoustic signal providing unit 110 may comprise a wearable transducer and a microphone.

It is also foreseen however, that acoustic signal providing unit 110 does not acquire the acoustic signal itself (e.g., by means of a microphone as proposed herein above). To this extent, acoustic signal providing unit 110 may comprise an input unit configured to receive said acoustic signal.

Figure 2:
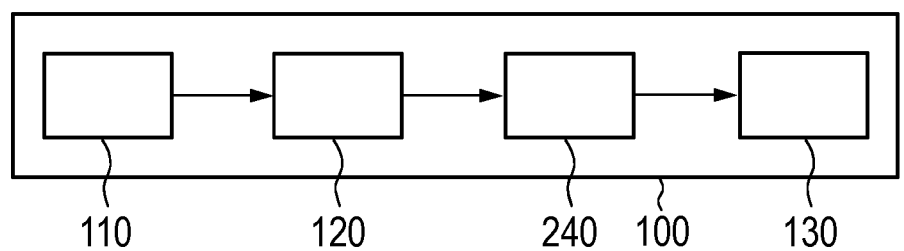
FIG. 2 shows schematically and exemplarily a further embodiment of a monitoring system.

FIG. 2 shows schematically and exemplarily an embodiment of monitoring system 100, wherein monitoring system 100 further comprises an optional calibration unit 240 that is configured to assign said at least one detection signal component to at least one reconstructed physiological or noise signal. Assigning said at least one detection signal component to at least one reconstructed physiological signal has to be understood as a mapping that can be performed based on correlation or similarity of the one said detection signal components or features of said one detection signal component with the calibration signal or features of the calibration signal, where features could be for example the signal strength and frequency. Another mapping construction method is searching from a variety of mappings such the resulting reconstructed physiological signal or features of the reconstructed physiological signal have maximum similarity or correlation to the calibration signal or features of the calibration signal.

Figure 3:
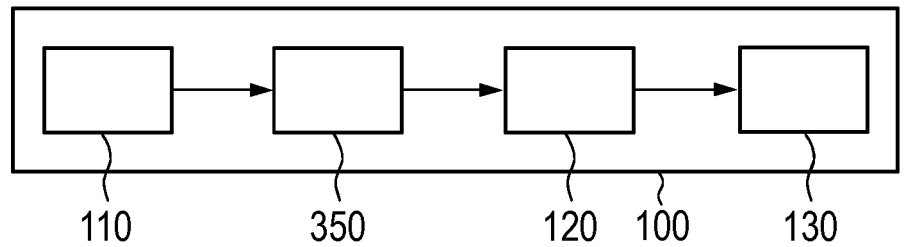
FIG. 3 shows schematically and exemplarily a further embodiment of a monitoring system.

FIG. 3 shows schematically and exemplarily an embodiment of monitoring system 100, wherein monitoring system 100 further comprises an optional feature extraction unit 350 configured to provide said detection signal. Monitoring system 100 may also comprise both of calibration unit 240 and feature extraction unit 350.

Feature extraction unit 350 may be configured to perform a discrete Fourier transform. Feature extraction unit 350 may further be configured to average absolute values of a plurality of frequency bins, wherein said plurality of frequency bins is obtained from performing said discrete Fourier transform. Feature extraction unit 350 may alternatively and/or additionally be configured to average squared values of a plurality of frequency bins, wherein said plurality of frequency bins is obtained from performing said discrete Fourier transform.

Figure 4:
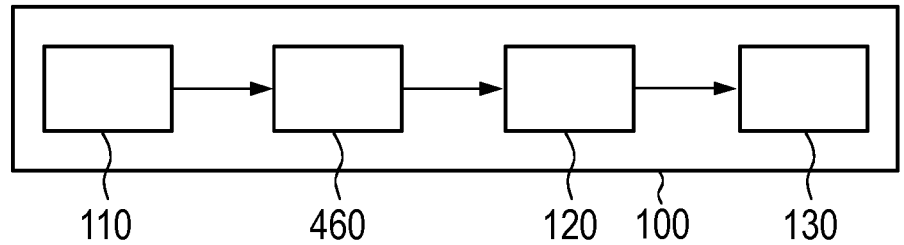
FIG. 4 shows schematically and exemplarily a further embodiment of a monitoring system.

FIG. 4 shows schematically and exemplarily an embodiment of monitoring system 100, wherein monitoring system 100 further comprises an optional pre-processing unit 460 configured to receive said acoustic signal. Monitoring system 100 may also comprise all or just some of calibration unit 240, feature extraction unit 350, and pre-processing unit 460.

Pre-processing unit 460 may be configured to perform a down-sampling step on said acoustic signal. Pre-processing unit 460 may comprise a high-pass filter unit configured to apply a high-pass filter to a signal obtained from said down-sampling step.

Figure 5:
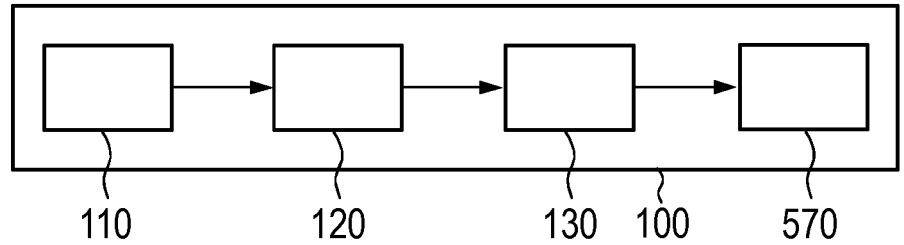
FIG. 5 shows schematically and exemplarily a further embodiment of a monitoring system.

FIG. 5 shows schematically and exemplarily an embodiment of monitoring system 100, wherein monitoring system 100 further comprises an optional display unit 570 configured to display at least one of said acoustic signal and said at least one reconstructed physiological or noise signal. Monitoring system 100 may also comprise all or just some of calibration unit 240, feature extraction unit 350, pre-processing unit 460, and display unit 570.

Figure 6:
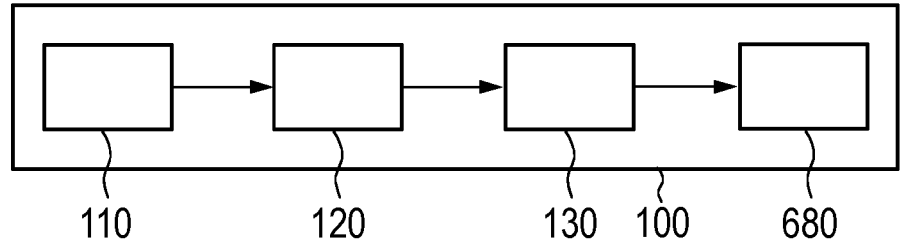
FIG. 6 shows schematically and exemplarily a further embodiment of a monitoring system.

FIG. 6 shows schematically and exemplarily an embodiment of monitoring system 100, wherein monitoring system 100 further comprises an optional storage unit 680 configured to store at least one of said acoustic signal and said at least one signal component. Monitoring system 100 may also comprise all or just some of calibration unit 240, feature extraction unit 350, pre-processing unit 460, display unit 570, and storage unit 680.

Figure 7:
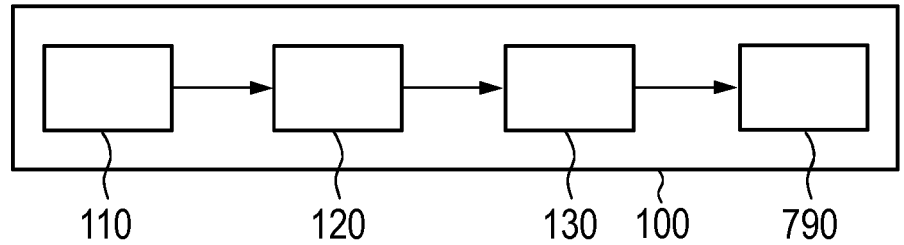
FIG. 7 shows schematically and exemplarily a further embodiment of a monitoring system.

FIG. 7 shows schematically and exemplarily an embodiment of monitoring system 100, wherein monitoring system 100 further comprises an optional reconstructed physiological or noise signal providing unit 790 configured to provide said at least one reconstructed physiological or noise signal. Monitoring system 100 may also comprise all or just some of calibration unit 240, feature extraction unit 350, pre-processing unit 460, display unit 570, storage unit 680, and reconstructed physiological or noise signal providing unit 790. Reconstructed physiological signal providing unit 790 may comprise an output unit.

Figure 8:
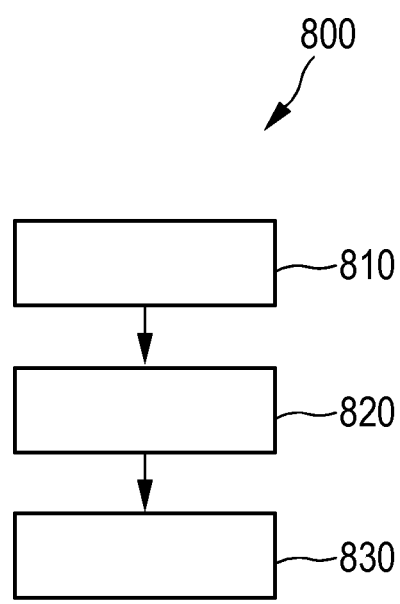
FIG. 8 shows schematically and exemplarily an embodiment of a monitoring method.

FIG. 8 shows schematically and exemplarily an embodiment of a monitoring method 800. In a step 810, an acoustic signal indicative of at least one physiological variable of a subject is provided. In a step 820, a detection signal is decomposed into at least one detection signal component, wherein said detection signal is based on said acoustic signal. In a step 830, said at least one physiological variable is derived from at least one reconstructed physiological signal, wherein said reconstructed physiological signal is based on said at least one detection signal component.

The acoustic signal may be acquired on the chest of a subject by means of a wearable transducer. As an example, a capture system may include a tiny (2.59×2.59 mm) cylindrically-shaped microphone placed in the aluminum chest piece of a single-head low-cost stethoscope. The microphone may provide with RFI suppression. The lightweight and flat stethoscope chest piece may be attached by double-sided medical adhesive tape rings to the upper-left side of the chest for continuous monitoring. In the case of a spot check measurement the chest piece may be held in place for the time needed.

The audio signal extracted can be modeled as:

$$a(t) = l(t) + h(t) + \sum_{i=1}^{p} n_i(t),$$

where a(t) is the signal recorder at the chest-wall, l(t) is the component related to the lung sounds, h(t) is the component related to the heart sounds, $$\sum_{i=1}^{p} n_i(t)$$

are the noise components related to biological interferences (as wheezes, crackles, swallowing sounds, etc.) and non-biological interferences (as 60 HZ, environment noise, etc.), t denotes time. It is noted that the parameter p is not necessarily known.

Figure 9:
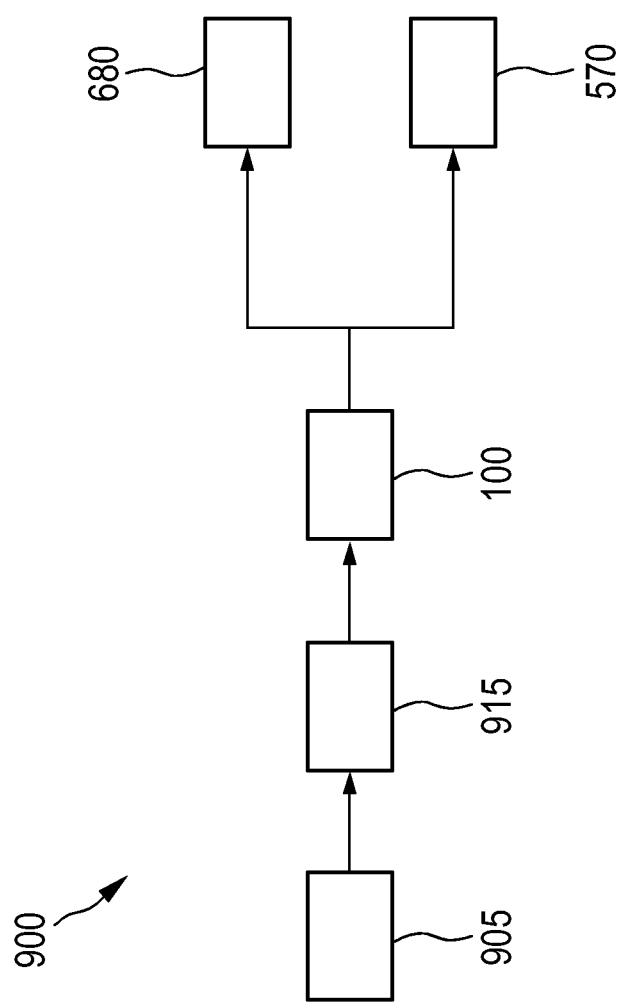
FIG. 9 shows schematically and exemplarily an embodiment of a monitoring arrangement.

FIG. 9 shows schematically and exemplarily an embodiment of monitoring arrangement 900. The acoustic signal is acquired by one or more sensors 905 attached to a patient's chest and subsequently transferred, e.g., via standard audio connectors 915, to monitoring system 100 where it may be down-sampled and processed as described above. Monitoring system 100 computes features from the original audio signal, and extracts, by means of decomposition techniques, a number of time series that represent different detection signal components of the detection signal based on the original acoustic signal. These different detection signal components are combined to create reconstructed physiological signals, which are used to extract physiological variables (e.g. respiratory and cardiac parameters) that may be stored in storage 680 and/or displayed on screen 570 of monitoring arrangement 900.

Figure 10:
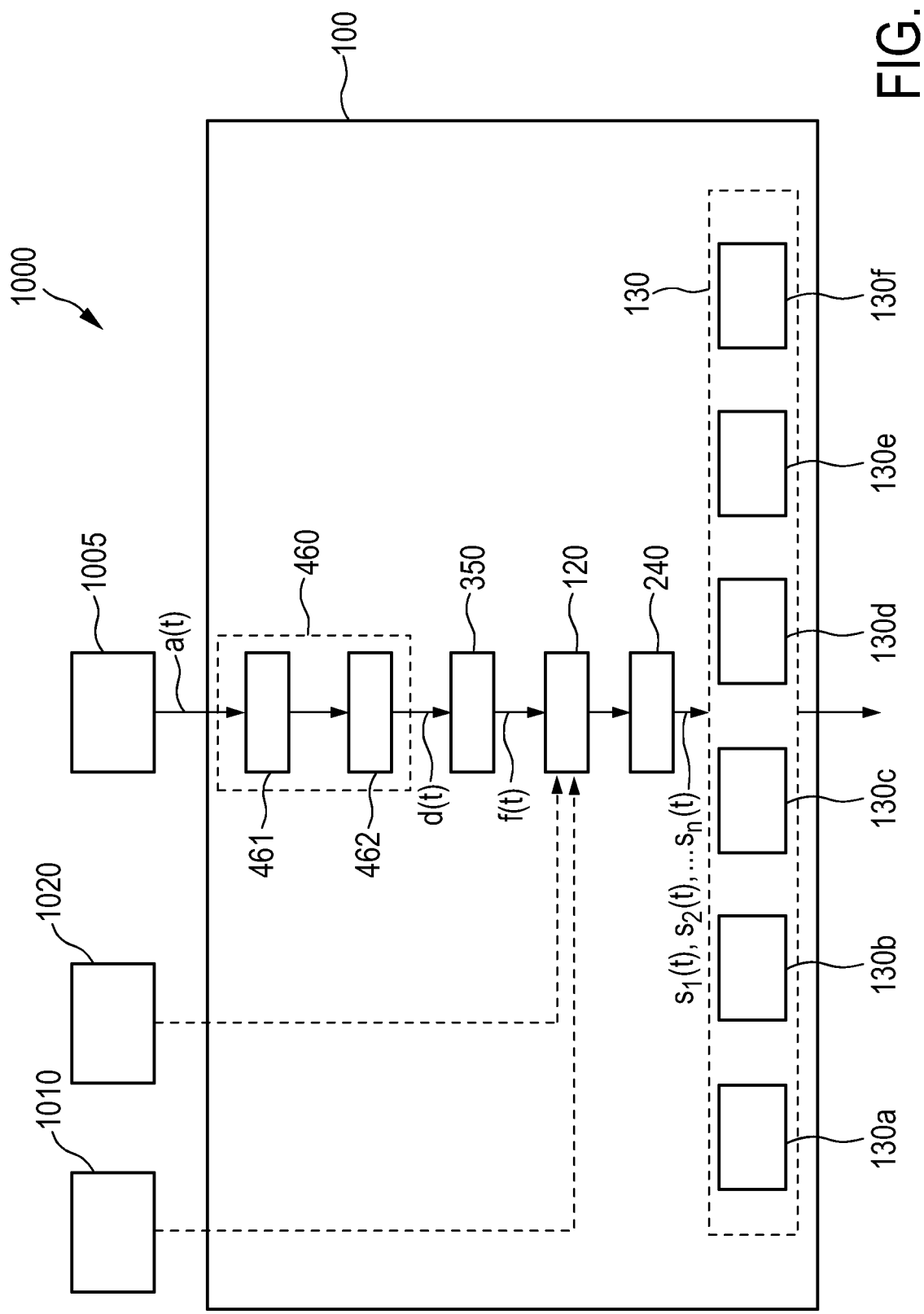
FIG. 10 shows schematically and exemplarily a further embodiment of a monitoring arrangement.

FIG. 10 shows schematically and exemplarily an embodiment of monitoring arrangement 1000 comprising an embodiment of monitoring system 100. The acoustic signal a(t) is acquired by an acoustic sensor 1005 placed on the chest of a subject and provided to monitoring system 100 by means of an input port (not shown), which in the present embodiment may be considered an example for acoustic signal providing unit 110 described above. The acoustic signal a(t) is first pre-processed by pre-processing unit 460 to reduce the computational complexity of the further steps. As an example, an audio signal acquired at 44 kHz can be down-sampled to 4 kHz by down-sampling unit 461. High-pass filter unit 462 attenuates low-frequency signals, e.g., with frequencies lower than 50 Hz. The resulting signal is denoted as d(t).

When observing the temporal evolution of the breathing signal, it is noticeable that the occurrence of an onset is usually accompanied by an increase of the signal's amplitude. Chest audio signals are both additive (lung, heart sounds and interferences superimpose rather than conceal each other) and oscillatory. Therefore, it is not possible to look for changes by simply differentiating the original signal in the time domain. A number of intermediate signals or features $f_i(t)$ that reflect, in a simplified form, the local structure of the original signal need to be computed for further processing. The result of said further processing is a detection signal f(t). In this embodiment, a feature extraction unit provides $f_i(t)$ as the DFT of the audio signal, but it can be replaced by any detection signal, by replacing the DFT computation by another computational module. For instance, other spectral representation like the Mel Frequency Cepstral Coefficients may be used as well.

Feature vector $f_i(t)$ is a function of time, but it typically has a sampling rate which is much lower than the sampling rate of the down-sampled acoustic signal. For instance, the discrete Fourier transform of the digitalized and down-sampled sound signal d(t) can be calculated using the Goertzel algorithm in Hanning windows of 25 ms with 50% overlap between the successive windows. The DFT is calculated specifying a frequency range of 100 to 800 Hz and a bin resolution of 5 Hz. The specified frequencies are rounded to the nearest DFT bin commensurate with the signal's resolution. A total of 141 individual terms corresponding to the 141 frequency bins in the range 100 to 800 Hz are then computed for each window and averaged to create the feature vector $f_i(t)$ with a resulting sampling rate of 79 Hz, which is enough to represent respiratory and cardiac signals. In the time-series of features extracted from the chest audio signal, all relevant information about the components of the original acoustic signal a(t) is still preserved. In this case, the feature vector is reduced to a single component, i.e., a single value per sampled time instant and therefore the index i is omitted in the remainder.

Feature vector f(t) is then processed by detection signal decomposition unit 120 that divides it into a number of additive time series, each of which can be easily identified as being part of the signals of interest (respiratory and cardiac signals), or as being part of the interferences. It is noted that detection signal decomposition unit 120 may receive and process information from optional further sensors 1010. Optional further sensors 1010 may involve an accelerometer that is capable to detect the body posture or the activity performed, internal sensors of a smartphone, or the entire smartphone itself. It is further noted that detection signal decomposition unit 120 may receive and process information from optional prior knowledge unit 1020. For instance, prior knowledge unit 1020 may provide information acquired during a calibration procedure in order to find those detection signal components, which are useful for reconstructing the respiratory signal and/or the cardiac signal. Prior knowledge unit 1020 may further provide boundary information such as, e.g., that if the subject is resting the breathing should show also a pause phase in between expiration and inspiration. Assigning the detection signal components to respective reconstructed physiological signals may be performed by optional calibration unit 240.

One possible decomposition technique used in this embodiment is the singular spectral analysis (SSA) because of its generality and ease to use in an automatic procedure. SSA indeed requires the selection of just one parameter: the window length L where to calculate the components. Other decomposition techniques such as, e.g. Empirical Mode Decomposition (EMD), might be used.

The decomposed signals are then grouped in order to reconstruct meaningful signals for further analysis: the reconstructed physiological and noise signals; some decomposed signal components may be discarded altogether. In particular, the reconstructed physiological signal $s_1(t)$ represents an estimate of the flow with positive (negative) peaks corresponding to the points of maximum inspiratory (expiratory) flow. Information about the respiration markers is captured in the zero crossings.

A zero crossing occurring with the sign of the signal changing from positive to negative corresponds to an expiration phase onset; on the other hand, a zero crossing with a sign change from negative to positive corresponds to an inspiration onset. The reconstructed physiological signals $s_2(t)$, $s_3(t)$, $s_4(t)$ and $s_6(t)$ represent respiratory signals with minima marking the respiration onsets and maxima marking the point of maximum flow.

The reconstructed physiological signal $s_5(t)$ corresponds to the cardiac signals where maxima are located in correspondence of the heart beat sounds. One or more of the resulting signals is input to dedicated estimation units 130a, ..., 130f of physiological variable providing unit 130. Dedicated estimation units 130a, ..., 130f output a number of physiologic parameters related to the respiratory and cardiac activity.

The units can be conceptually separated, but they may be just as well be realized as a single unit. Units 130a, ..., 130f may also be configured in such a way that some of the blocks are operating in a continuous monitoring mode, while other blocks are executed at particular times only, e.g., triggered by the user or another trigger.

Examples for estimation units are the respiration rate (RR) unit 130a which calculates the instantaneous respiration rate and breathing markers unit 130b which calculates time markers for e.g., inspiration and expiration onsets. Heart rate (HR) unit 130c uses predominantly the reconstructed physiological signal $s_5(t)$ to determine the heart rate and/or comparable or derived measures like interbeat intervals or heart rate variability. Cough detection unit 130d picks up one or more decomposed signal parts to detect cough occurrences. It outputs e.g., cough time stamps or cough rates. Abnormal sounds unit 130e detects if there are abnormal sounds. If this is the case, time markers may be generated signaling the occurrence, the frequency of these occurrences may be calculated and sound snippets may be stored for later inspection by a doctor. Flow estimation unit 130f estimates the flow rate by the use of the signals related to the respiration behavior. Integration with the original audio signal and the detection function may also be used.

Figure 11:
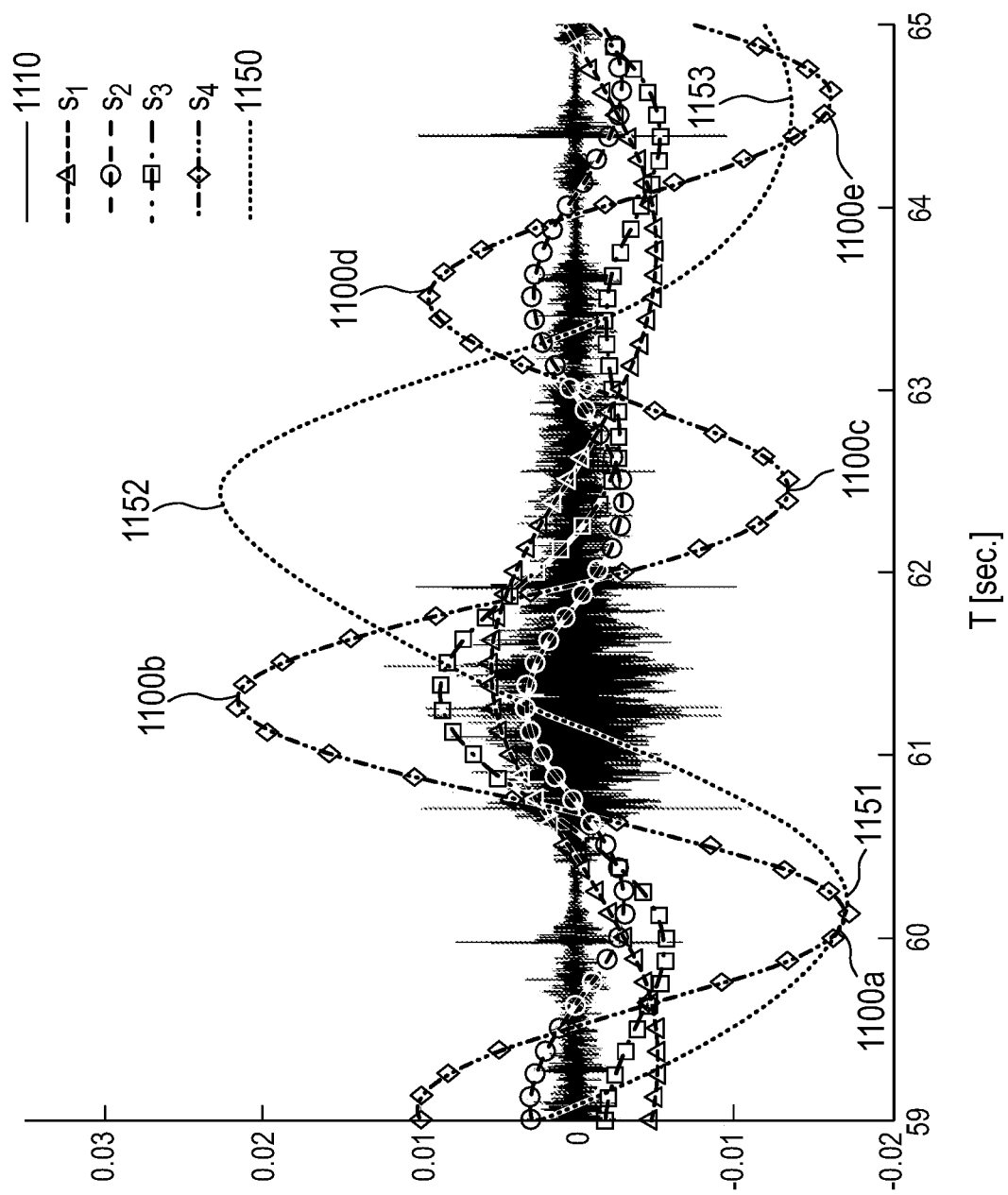
FIG. 11 shows schematically and exemplarily example reconstructed physiological signals together with an acoustic signal and a reference signal.

FIG. 11 shows schematically and exemplarily reconstructed physiological signals $s_1(t)$, $s_2(t)$, $s_3(t)$ and $s_4(t)$ together with acoustic signal 1110 and reference signal 1150. In the example shown, reference signal 1150 may be obtained from a chest band measuring the chest expansion to thereby distinguish inspiration and expiration phases. In the example shown, the start of an inspiration phase is indicated by reference signal minima 1151, 1153, whereas the end of an inspiration phase (and start of an expiration phase) is indicated by reference signal maximum 1152. From the markers and the reconstructed signal waves, the variables of interest such as, e.g., respiration rate, phase duration, and flow can be estimated. In particular, the maxima (minima) in the reconstructed physiological signal $s_1(t)$ correspond to the maximal inspiratory (expiratory) flow peaks. The minima in the reconstructed physiological signals $s_2(t)$, $s_3(t)$ and $s_4(t)$ correspond to the onsets of the breathing, the maxima to the maximal flow peaks. From the said reconstructed physiological signals $s_1(t)$, $s_2(t)$, $s_3(t)$ and $s_4(t)$, markers 1100a, ..., 1100e are determined which may in turn be used to derive the respective beginnings and endings of inspiration and expiration phases. In the example shown, markers 1100a, ..., 1100e correspond to respective maxima and minima of the reconstructed physiological signals $s_2(t)$, $s_3(t)$ and $s_4(t)$. From the signal component amplitude at a respective marker location, it may then be determined whether, e.g., a marker indicates the beginning of an inspiration phase (corresponding to a large amplitude) or the beginning of an expiration phase (corresponding to a smaller amplitude). Namely, by calculating marker 1100*a* from acoustic signal 1110, the beginning of an inspiration phase may be derived. Marker 1100*b* labels a local maximum of the inspiration flow. Next, by calculating marker 1100*c* from acoustic signal 1110, the beginning of an expiration phase may be derived. Marker 1100*d* labels a local maximum of the expiration flow. Next, by calculating marker 1100*e* from acoustic signal 1110, the beginning of another inspiration phase may be derived.

Figure 12:
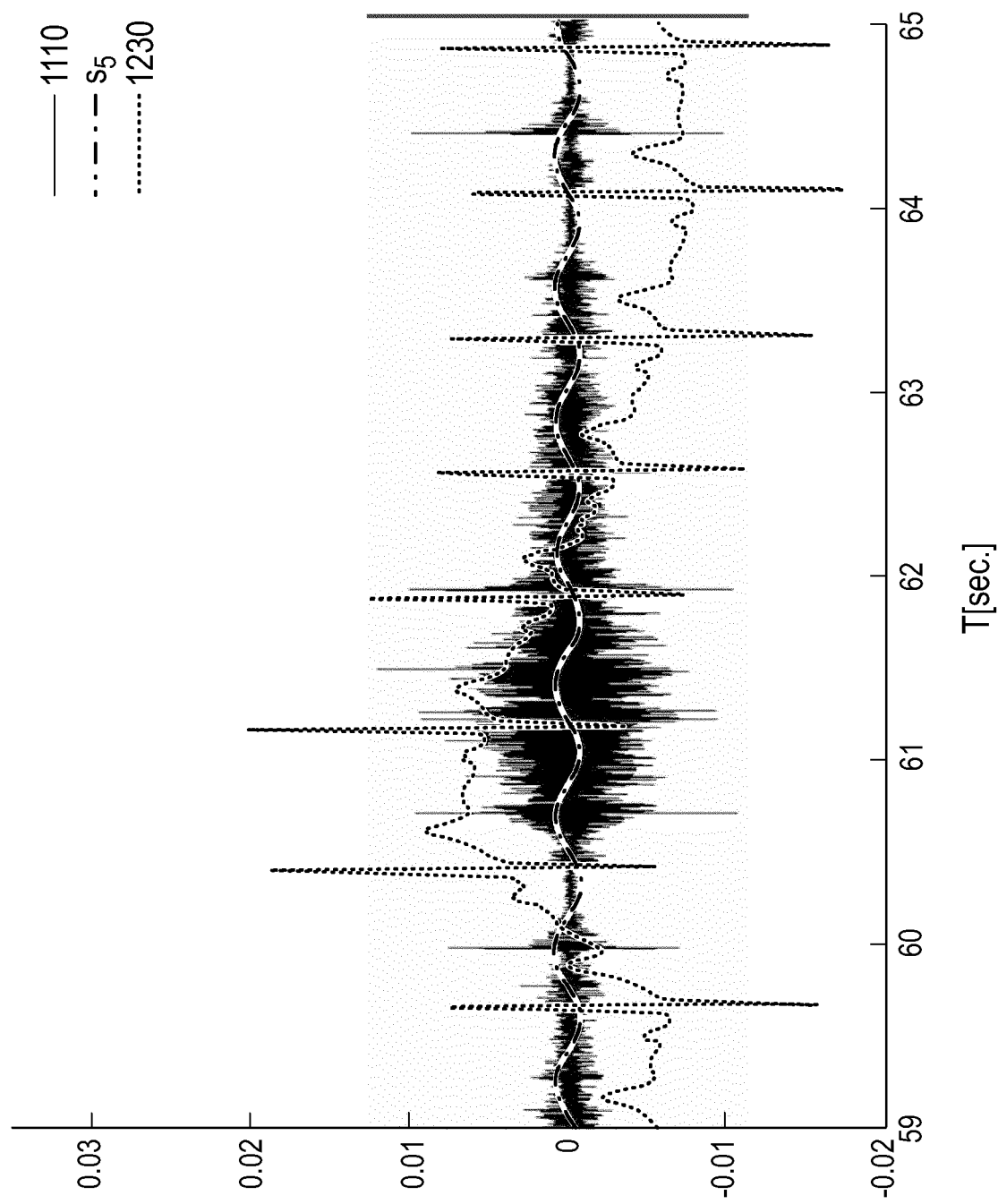
FIG. 12 shows schematically and exemplarily example reconstructed physiological signal together with an acoustic signal and a reference signal.

FIG. 12 shows schematically and exemplarily the reconstructed physiological signal $s_5(t)$ together with acoustic signal 1110 and reference signal 1230. In the example shown, reference signal 1230 may be obtained by measuring an ECG. In the example shown, local maxima of reconstructed physiological signal $s_5(t)$ indicate the heart sounds from which it is possible to estimate the heart rate.

Figure 13:
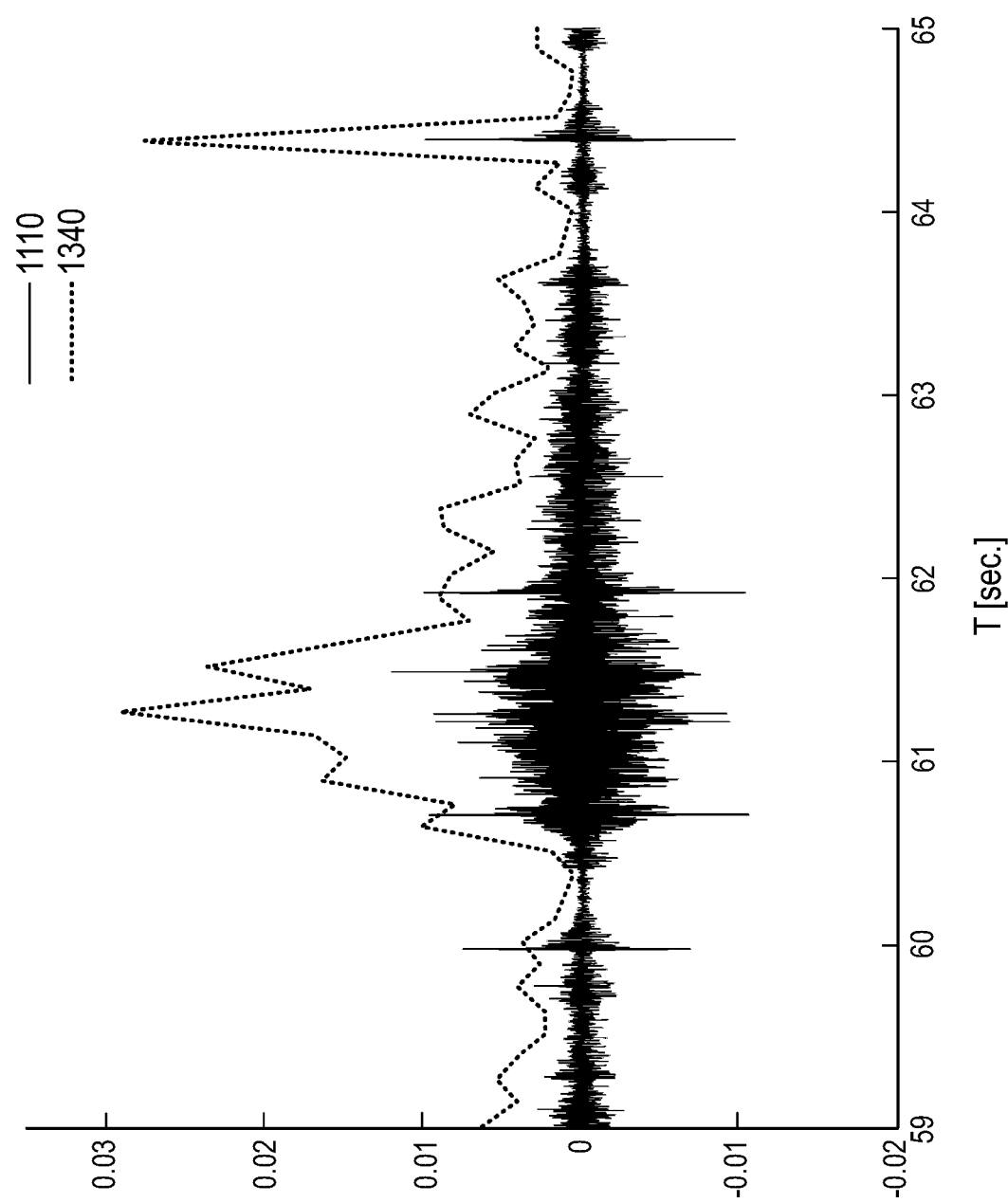
FIG. 13 shows schematically and exemplarily a detection signal together with an acoustic signal.

FIG. 13 shows schematically and exemplarily a reconstructed detection function 1340 together with acoustic signal 1110. The peaks around ca. 61.3 sec correspond both to the maximum inspiratory flow peak 1100*b* in FIG. 11 (loudest moment during the inspiratory phase). Second and third peaks of the detection function around ca. 61.5 and 64.5 sec correspond to the S2 cardiac sound reflecting the closure of the semilunar valves and visible in the ECG in correspondence of the T wave.

Figure 14:
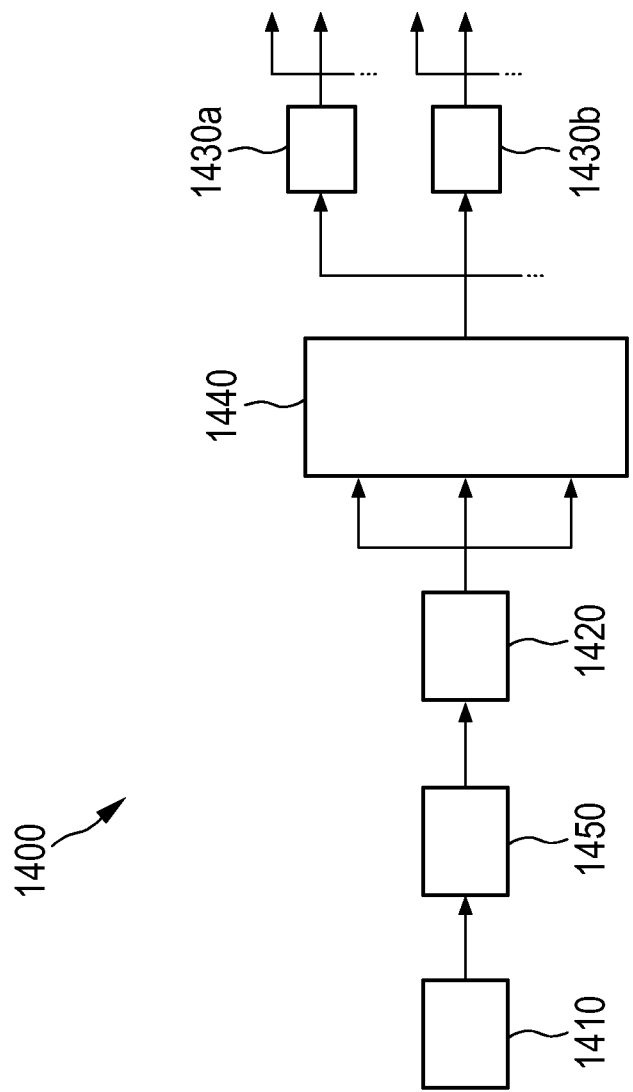
FIG. 14 shows schematically and exemplarily a further embodiment of a monitoring system.

FIG. 14 shows schematically and exemplarily a further embodiment of a monitoring system 1400. An audio signal is output from acoustic signal providing unit 1410 and provided to feature extraction unit 1450. Feature extraction unit 1450 extracts a detection signal and provides the same to decomposition unit 1420. Decomposition unit 1420 may perform, e.g., an SSA algorithm. Decomposition unit 1420 provides detection signal components to calibration unit 1440. Calibration unit 1440 provides reconstructed physiological and noise signals to physiological providing units 1430*a*, 1430*b*, . . . Physiological providing units 1430*a*, 1430*b*, . . . then provide the desired physiological variables.

An example application of the invention is in any chest based system, intended to compute estimates of respiration and cardiac parameters in unhealthy subjects, where extended models are needed to cope with abnormalities that might be found in the acoustic signal under examination. It is assumed that the invention may be used with healthy subjects as well. With the proposed system and methodology a general alternative to the use of dedicated and complex filter banks is presented. The system and methodology proposed require a minimum setting of parameters and may be used without knowing the exact number or nature of interferences present in the signal acquired. Strength of the system is its portability and minimum obstructiveness.

A further example application of the invention is in continuous patient monitoring including: home monitoring of a patient's vital signs, hospital monitoring of a patient's vital signs, robust and affordable automated respiratory rate monitors to support the diagnosis of pneumonia among infants and children.

A further example application of the invention is in spot-check patient monitoring including: an extension of a vital signs camera application, dyspnea score calculation, and breathing techniques teaching system. Trends in respiration rate and TI/TE ratio may also be instructive in some applications as for teaching breathing strategies. Direct emphasis on the breathing parameter (in particular on the expiratory time) may be more effective compared with the usual teaching instructions to increase VT or slow RR, since prolonged expiratory times in relation to inspiratory times would likely decrease air trapping and reduce dynamic hyperinflation for those with obstructive ventilatory disorders and provide dyspnea relief.

A further example application of the invention is in the context of a caregiver/nurse decision support system including connecting the transducer and downloading a dedicated smartphone application, so that any smartphone could become a low cost electronic stethoscope. This could be used for a first automatic screening of stationary patients or to support nurses' decision making (identification and classification of adventitious breath sounds, blood pressure detection system).

A further example application of the invention is in the context of a self-care processes support system keeping an automatic symptoms diary (such as, e.g., number of cough events, snoring events, HR, RR, etc.). For disease of minor importance like seasonal cough and fever, people (especially young people) often refrain from calling the doctor thinking that the symptoms will end in a couple of days. This behavior is caused for the most part by the lack of time for going to the doctor. The present invention could be used to develop a system that: (1) asks the patient (or another person on his behalf) to record breathing sounds (from different positions in the chest) using a stethoscope connected to a smartphone; (2) asks to compile a symptom-form (temperature, symptoms, etc.); (3) sends the acquired data via e-mail to the doctor.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems. The term "computer program" may also refer to embedded software.

Any reference signs in the claims should not be construed as limiting the scope.

The present invention relates to a system and method capable of indirectly monitoring respiratory and cardiac variables. A decomposition technique on time-series of features extracted from the chest audio signal is proposed. The proposed system may acquire the acoustic signal on the chest of a subject by means of a wearable transducer. The proposed system may estimate a number of physiological variables such as respiration rate, inspiration and expiration markers and cardiac related variables. Cough and apnea detection, adventitious sound recognition, activities performed, and information about the status of a monitored subject can be derived as well.

The invention claimed is:

1. A respiration monitoring system comprising:
an acoustic signal providing unit comprising an acoustic sensor structured to be coupled to a chest of a subject for providing an acoustic signal indicative of at least one physiological variable of the subject, a computer in communication with the acoustic signal providing unit, wherein the computer includes:
  a feature extraction unit that is configured to provide a detection signal based on a spectral analysis of the acoustic signal, wherein said detection signal is a signal in a time domain that reflects a local structure of the acoustic signal in a simplified form;
  a detection signal decomposition unit that is configured to decompose the detection signal into at least one detection signal component; and
  a physiological variable providing unit that is configured to derive said at least one physiological variable from at least one reconstructed physiological signal, wherein said at least one reconstructed physiological signal is based on said at least one detection signal component,
  wherein said detection signal decomposition unit is configured to decompose said detection signal such that a decomposition of said detection signal is data-driven and includes at least one of a singular spectral analysis and/or an empirical mode decomposition,
  wherein the feature extraction unit is configured to provide the detection signal based on spectral representations of the acoustic signal by averaging values of a plurality of frequency bins obtained from the spectral representations, and
  wherein the spectral representations are created from the acoustic signal using successive and overlapping windows.

2. The monitoring system as defined in claim 1, wherein said computer further comprises a pre-processing unit configured to receive said acoustic signal, wherein said pre-processing unit is configured to perform a down-sampling step on said acoustic signal, wherein said pre-processing unit comprises a high-pass filter unit configured to apply a high-pass filter to a signal obtained from said down-sampling step.

3. The monitoring system as defined in claim 1, wherein said computer further comprises a display unit configured to display at least one of said acoustic signal, said at least one detection signal component, and/or said at least one reconstructed physiological signal.

4. The monitoring system as defined in claim 1, wherein said computer further comprises a storage unit configured to store at least one of said acoustic signal, said at least one detection signal component and/or said at least one reconstructed physiological signal.

5. The monitoring system as defined in claim 1, wherein the feature extraction unit is configured to provide the detection signal by averaging absolute values of the plurality of frequency bins or by averaging squared values of the plurality of frequency bins.

6. The monitoring system as defined in claim 1, wherein the detection signal includes a single value per sampled time instant.

7. A monitoring method comprising:
  providing an acoustic signal indicative of at least one physiological variable of a subject from an acoustic sensor structured to be coupled to the subject's chest,
  providing a detection signal based on a spectral analysis of the acoustic signal, wherein said detection signal is a signal in a time domain that reflects a local structure of the acoustic signal in a simplified form;
  decomposing the detection signal into at least one detection signal component; and
  deriving said at least one physiological variable from at least one reconstructed physiological signal, wherein said at least one reconstructed physiological signal is based on said at least one detection signal components
  wherein the providing of the detection signal is based on a spectral representation of the acoustic signal by averaging values of a plurality of frequency bins obtained from the spectral representation, and
  wherein the spectral representations are created from the acoustic signal using successive and overlapping windows.

8. A non-transitory computer readable medium comprising:
  instructions for causing a monitoring system to carry out the monitoring method as defined in claim 7.

* * * * *